United States Patent [19]

Barna

[11] 3,960,724
[45] June 1, 1976

[54] PROCESS FOR THE SEPARATION OF NATURAL WATER-SOLUBLE ALUMINUM HYDROSILICATE ORGANO-COMPLEXES

[75] Inventor: Janos Barna, Budapest, Hungary

[73] Assignee: Novex Találmányfejlesztó és Értékesitó Külkereskedelmi Rt., Budapest, Hungary

[22] Filed: May 22, 1974

[21] Appl. No.: 472,508

[52] U.S. Cl. .................................... 210/49; 209/5
[51] Int. Cl.² .................................... B01D 43/00
[58] Field of Search ............ 210/49, 47, 42, 51–54, 210/59; 209/5

[56] References Cited
UNITED STATES PATENTS

| | | | |
|---|---|---|---|
| 1,526,971 | 2/1925 | Feldenheimer | 209/5 |
| 3,617,561 | 11/1971 | Fanselow | 210/47 |

*Primary Examiner*—Thomas G. Wyse
*Attorney, Agent, or Firm*—Young & Thompson

[57] ABSTRACT

Peptisable natural aluminum hydrosilicate organo complexes are separated from water-insoluble organic and/or inorganic mineral materials and from natural aluminum hydrosilicate organo complexes that cannot be peptised in water, by milling mineral materials such as clay or brown coal to a size smaller than 60 microns, vigorously mechanically agitating the mixture at 60 to 120° C. so as to dissociate the same to the colloidal state, during which the hydrophilic binding positions of the material are loosened by hydration, and finally separating the thus-formed peptised solution from insoluble material. The solution may be concentrated and the insoluble material itself is useful because of increased calorific value and higher specific surface area. Peptisation may be carried out in the presence of peptising agents such as ammonia-soda, $Na_2CO_3$, $NaOH$, $KOH$, or cetyl-pyridine-chloride, in an amount up to 5% by weight.

4 Claims, No Drawings

PROCESS FOR THE SEPARATION OF NATURAL WATER-SOLUBLE ALUMINUM HYDROSILICATE ORGANO-COMPLEXES

The invention concerns a process for the separation of natural water-soluble, aluminium hydrosilicate organo-complexes from water-insoluble organic and/or inorganic mineral substances, and from water-insoluble aluminium hydrosilicate organo-complexes.

Synthetic organic clay minerals have been treated primarily by Jordan whose work initiated the manufacture of the so-called organophilic bentonite. He showed that with organic compounds having from six carbon atoms upwards the formation of organo-complexes starts, which complexes precipitate in water and swell in organic solvents.

In nature, dilute sols of clays and very fine dispersions undergo the colloidal process of "carbonization", i.e. the taking up of organic materials. Organic substances with small molecules or having short chains, having fewer than six carbon atoms, produce water-soluble aluminium hydrosilicate organo-complexes, while substances with larger molecules and longer chains produce water-insoluble aluminium hydrosilicate organo-complexes.

In the course of "carbonization" in nature, the water-soluble and water-insoluble aluminium hydrosilicate organo-complexes were intensively mixed in a colloidal dispersion of the "soluble" material and apparently homogeneous, multimillion-ton mineral reserves have been produced. In the absence of a separation process for the water-soluble aluminium hydrosilicate organo-complexes, this mineral wealth could not even be recognised. The most typical aluminium hydrosilicates, the clays, have a strongly limited colloidal solubility in water. Colloidal solubility depends primarily on the morphological properties of the aluminium hydrosilicates, but it depends also on the specific surface area that can be attained on dispersing them in water.

It is also well-known that from the point of view of soil cultivation all clays are useful in proportion to the amount of organic material they contain in complex binding, since in that way they exert a favourable influence on the physical properties of the soil and on the nutrient absorption of plants.

For a long time now experiments have been in progress in Hungary to turn to account brown coal (lignite) for agricultural, primarily soil improvement, purposes. Thus in an experimental plant humic acid is being produced by treating brown coal with potassium hydroxide solution. In this process 20 % by weight KOH (relative to the amount of coal), is required at a relatively high temperature. Experiments are also being carried out to nitrify brown coal with dilute nitric acid, or with concentrated nitric acid, optionally with additives, to produce fertiliser-like products.

The production of humic acid in the above-described manner for agricultural purposes is extremely expensive; furthermore, the alkaline or nitric acid treatment of brown coal is strongly corrosive. The product obtained has an uncertain effect: it has happened that the product does not stimulate the growth of plants but on the contrary inhibits germination.

Known attempts to improve the soil include scattering comminuted clay-containing hard coal of high ash-content, and the ploughing-in of such scattered material, so as to try to make the soil structure more favourable by adding organic substances in this way, all the more so since even very small amounts of organic substances can alter the physical properties of the soil. However, on formation, the aluminium hydrosilicate organo-complexes which are peptisable in water are occluded by water-insoluble aluminium hydrosilicates and are embedded in them as a colloidal enclosure. Experiments attempting to make use of the organic substances by scattering the coal in comminuted form on the soil have been unsuccessful.

Apart from agriculture, in numerous industrial fields there is a need for cheaply producible materials which have good solubility in water, are thixotropic and on drying have a binding property. Such materials are indispensable in water-based paints for walls to reduce precipitation or settlement, to effect the adhesion (binding), and wetting, and to fix the paint pigments more stably.

As carriers for many spray materials or other chemicals, clay minerals such as bentonite and kaolin have hitherto been employed. However, these minerals have to a large extent neutralised the activity of the spray material or its active substance. Thus in this field the need has also arisen for a carrier which does not adversely influence the effectiveness of the spray material or of the chemicals in it.

The aim of the invention is the separation of water-soluble aluminium hydrosilicate organo-complexes from water-insoluble, organic or inorganic mineral substances, and from water-insoluble aluminium hydrosilicate organo-complexes. This aim is attained by milling the mineral material to a size smaller than 60 microns, optionally adding, relative to the weight of the mineral, up to 5 % by weight of peptising agent, e.g. ammonia soda, $Na_2CO_3$, KOH, NaOH, or cetyl-pyridine-chloride, vigorously agitating mechanically e.g. at 60°–120°C, to dissociate to the colloidal state the mixture of organic complex materials, in the course of which the hydrophilic binding positions of the materials are loosened by hydration, and finally separating the thus formed peptised solution from insoluble materials.

The process according to the invention is in essence a mechano-chemical activation which results in the solvation of the dispersed particles.

The process according to the invention makes it possible to separate the water-soluble aluminium hydrosilicate organo-complexes which are produced by nature in multimillion-ton quantities and thus to open up an enormous mineral reserve.

It is a very significant property of clay mineral organo-complexes that can be peptised in water, that the concentration of the material that can be dissolved out reaches 15– 30 %. If these values are compared with the general solubility of less than 1 % of clay materials, except Hungarian allevardite which has a solubility of 4 % and bentonite from Mád which has a solubility of 2.5 %, it will be apparent that the organic compounds in a complex binding with the clay minerals have very considerably increased the peptisibility in water of the clay minerals.

The naturally occurring aluminium hydrosilicate complexes separable by the process according to the invention contain in a concentrated extract very important materials for the soil and thus the separated aluminium hydrosilicate complexes may be regarded as a soil conditioner. By their use one can simultaneously add the highly important clay minerals and approximately 20 % of organic material. It is of very great advantage that the organic material does not decompose in the soil, because the clay materials conserve it. A further advantage lies in that it stimulates the microflora of the soil.

The water-soluble natural aluminium hydrosilicate organo-complexes separated according to the process of the invention and in an aqueous solution form on the surface of sandy soil a strong film-forming layer and by virtue of their binding property protect the soil against wind erosion. The natural water-soluble aluminium hydrosilicate organo-complexes separated according to the process of the invention have little further chemical reaction with organic compounds and can be regarded as inactive complex material from the point of view that they are unavailable for making further complex bonds, the positions for complex bonding being occupied. The organic products of peptisation can therefore be regarded as inactive, which has a very great practical significance since the water-soluble, natural aluminium hydrosilicate organo-complexes isolated according to the invention may also be used as fillers. This property is of great significance in the filling of active organic substances, plant protecting agents, weed killers etc.

The water-soluble, aluminium hydrosilicate organo-complexes according to the invention in their aqueous solutions have considerable thixotropic properties and thus can be used as settlement-preventing materials wherever their darker colour permits this. The water-soluble clay material organo-complexes may be used as precipitating agents for the purification of drinking water or effluents by virtue of their great specific surface area.

The natural, clay material organo-complexes in colloidal solution may be used as, or as an improvement of, the flushing medium (drilling mud) in deep-boring because of their electrolytic and thermal stability and because of their favourable rheological properties.

A further advantage resides in that the water-soluble, natural, aluminium hydrosilicate organo-complexes isolated by the process according to the invention may be marketed, after concentration, in the form of a paste or, after spray-drying, in the form of a powder.

For soil improvement purposes they may be used by spraying in powder form or where the obtained complexes are dissolved, they may be sprinkled or introduced in an irrigation system.

When starting from brown coal the water-soluble natural materials arising as a by-product of the process according to the invention may be turned to account as enriched coal of considerably increased calorific value. Their higher specific surface area, which can reach the value of 200 to 300 m²/g, makes it possible also to employ the enriched coal particles as a filter aid.

Processes according to the invention are described in the Examples, applied to brown coal.

EXAMPLE 1

Brown coal from Mizserfa, Nógrád, Hungary having an ash content of 52 % and a peptisable part of 48 % by weight is milled to 60 micron particle size in a conventional way. Into a known desegregator 200 liters of water is placed, the machine is started up, and 150 kg of the milled coal milling are added. The desegregator is then operated in reverse for 5 minutes. Thereafter the slurry is dewatered in a filter press and the residue dried in air.

The aluminium hydrosilicate organo-complex solution obtained is concentrated, or by spray-drying formed into powder, by conventional means.

EXAMPLE 2

The dispersion prepared in Example 1 is diluted with 200 liters of water, is settled and the obtained solution collected in a separate container. The residue, the enriched coal, is dried and the solution treated as in Example 1.

EXAMPLE 3

In Example 1 the dispersion is effected with water at 80°C.

EXAMPLE 4

In the Examples 1 to 3, to facilitate peptisation, there is added ammonia-soda in the amount of 3 % relative to the weight of coal.

EXAMPLE 5

In the Example 1 to 3, 0.2 % of cetyl-pyridine-chloride is employed to stimulate peptisation.

For the desegregation and dispersion any suitable single-stage or multi-stage apparatus, colloidal mill, etc., may be used.

What we claim is:

1. A mechano-chemical activation process for the separation of peptisable natural aluminium hydrosilicate organo-complex from brown coal, characterized by milling brown coal to a size smaller than 60 microns, admixing the milled brown coal with water, vigorously mechanically agitating the mixture of brown coal and water at 60 to 120°C. so as to dissociate to the colloidal state, in the course of which the hydrophilic binding positions of the materials are loosened by hydration, and finally separating the thus-formed peptised solution from insoluble material.

2. A process according to claim 1, characterized in that the peptisation is carried out in the presence of organic and/or inorganic peptising agents in the amount of up to 5 % by weight.

3. A process according to claim 2 characterized in that as peptising agent an alkaline material selected from the group consisting of ammonia-soda, $Na_2CO_3$, NaOH and KOH is employed in an amount of up to 5% by weight.

4. A process according to claim 2 characterized in that cetyl-pyridine-chloride is employed as peptising agent.

* * * * *